(12) United States Patent
Shoemaker et al.

(10) Patent No.: US 8,052,914 B2
(45) Date of Patent: Nov. 8, 2011

(54) MODIFIED PLUG FOR ARTERIOTOMY CLOSURE

(75) Inventors: Susan M. Shoemaker, Elk River, MN (US); Jason P. Hill, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 408 days.

(21) Appl. No.: 12/390,067

(22) Filed: Feb. 20, 2009

(65) Prior Publication Data

US 2010/0217310 A1 Aug. 26, 2010

(51) Int. Cl.
*B29C 53/00* (2006.01)
*B29C 55/00* (2006.01)
*B29C 57/00* (2006.01)
*A61B 17/08* (2006.01)
*A61D 1/00* (2006.01)

(52) U.S. Cl. ......... 264/339; 264/296; 264/285; 606/213

(58) Field of Classification Search .................. None
See application file for complete search history.

(56) References Cited

U.S. PATENT DOCUMENTS

| | | | |
|---|---|---|---|
| 5,021,059 A | 6/1991 | Kensey et al. |
| 5,108,421 A | 4/1992 | Fowler |
| 5,129,882 A | 7/1992 | Weldon et al. |
| 5,192,300 A | 3/1993 | Fowler |
| 5,192,302 A | 3/1993 | Kensey et al. |
| 5,221,259 A | 6/1993 | Weldon et al. |
| 5,222,974 A | 6/1993 | Kensey et al. |
| 5,254,105 A | 10/1993 | Haaga |
| 5,275,616 A | 1/1994 | Fowler |
| 5,282,827 A | 2/1994 | Kensey et al. |
| 5,290,310 A | 3/1994 | Makower et al. |
| 5,292,332 A | 3/1994 | Lee |
| 5,310,407 A | 5/1994 | Casale |
| 5,312,435 A | 5/1994 | Nash et al. |
| 5,320,639 A | 6/1994 | Rudnick |
| 5,342,393 A | 8/1994 | Stack |
| 5,350,399 A | 9/1994 | Erlebacher et al. |
| 5,370,660 A | 12/1994 | Weinstein et al. |
| 5,383,896 A | 1/1995 | Gershony et al. |
| 5,383,899 A | 1/1995 | Hammerslag |
| 5,391,183 A | 2/1995 | Janzen et al. |
| 5,411,520 A | 5/1995 | Nash et al. |
| 5,413,571 A | 5/1995 | Katsaros et al. |
| 5,415,657 A | 5/1995 | Taymor-Luria |
| 5,419,765 A | 5/1995 | Weldon et al. |
| 5,437,631 A | 8/1995 | Janzen |
| 5,441,517 A | 8/1995 | Kensey et al. |
| 5,443,481 A | 8/1995 | Lee |
| 5,447,502 A | 9/1995 | Haaga |
| 5,454,833 A | 10/1995 | Boussignac et al. |
| 5,478,326 A | 12/1995 | Shiu |

(Continued)

FOREIGN PATENT DOCUMENTS

EP 1568326 A1 8/2005

(Continued)

*Primary Examiner* — Christina Johnson
*Assistant Examiner* — Benjamin Schiffman
(74) *Attorney, Agent, or Firm* — Seager, Tufte & Wickhem, LLC

(57) ABSTRACT

The disclosure provides a modified arteriotomy closure plug, the modification consisting of subjecting a bioabsorbable foam closure plug to radial compression and/or axial bending until at least some struts of the foam have been torn or elongated within at least one axially disposed region.

11 Claims, 5 Drawing Sheets

U.S. PATENT DOCUMENTS

| | | |
|---|---|---|
| 5,478,352 A | 12/1995 | Fowler |
| 5,486,195 A | 1/1996 | Myers et al. |
| 5,529,577 A | 6/1996 | Hammerslag |
| 5,531,759 A | 7/1996 | Kensey et al. |
| 5,540,715 A | 7/1996 | Katsaros et al. |
| 5,545,178 A | 8/1996 | Kensey et al. |
| 5,549,633 A | 8/1996 | Evans et al. |
| 5,571,181 A | 11/1996 | Li |
| 5,573,518 A | 11/1996 | Haaga |
| 5,591,204 A | 1/1997 | Janzen et al. |
| 5,593,422 A | 1/1997 | Muijs Van de Moer et al. |
| 5,601,602 A | 2/1997 | Fowler |
| 5,613,974 A | 3/1997 | Andreas et al. |
| 5,620,461 A | 4/1997 | Muijs Van De Moer et al. |
| 5,626,601 A | 5/1997 | Gershony et al. |
| 5,630,833 A | 5/1997 | Katsaros et al. |
| 5,649,959 A | 7/1997 | Hannam et al. |
| 5,653,730 A | 8/1997 | Hammerslag |
| 5,662,681 A | 9/1997 | Nash et al. |
| 5,676,689 A | 10/1997 | Kensey et al. |
| 5,700,277 A | 12/1997 | Nash et al. |
| 5,707,393 A | 1/1998 | Kensey et al. |
| 5,716,375 A | 2/1998 | Fowler |
| 5,725,498 A | 3/1998 | Janzen et al. |
| 5,725,551 A | 3/1998 | Myers et al. |
| 5,728,114 A | 3/1998 | Evans et al. |
| 5,728,122 A | 3/1998 | Leschinsky et al. |
| 5,728,133 A | 3/1998 | Kontos |
| 5,728,134 A | 3/1998 | Barak |
| 5,741,223 A | 4/1998 | Janzen et al. |
| 5,782,860 A | 7/1998 | Epstein et al. |
| 5,810,884 A | 9/1998 | Kim |
| 5,830,130 A | 11/1998 | Janzen et al. |
| 5,843,124 A | 12/1998 | Hammerslag |
| 5,853,421 A | 12/1998 | Leschinsky et al. |
| 5,861,004 A | 1/1999 | Kensey et al. |
| 5,871,474 A | 2/1999 | Hermann et al. |
| 5,871,501 A | 2/1999 | Leschinsky et al. |
| 5,906,631 A | 5/1999 | Imran |
| 5,916,236 A | 6/1999 | Muijs Van de Moer et al. |
| 5,922,009 A | 7/1999 | Epstein et al. |
| 5,935,147 A | 8/1999 | Kensey et al. |
| 5,947,997 A | 9/1999 | Pavcnik et al. |
| 5,948,425 A | 9/1999 | Janzen et al. |
| 5,951,583 A | 9/1999 | Jensen et al. |
| 5,957,952 A | 9/1999 | Gershony et al. |
| 6,007,561 A | 12/1999 | Bourque et al. |
| 6,017,359 A | 1/2000 | Gershony et al. |
| 6,045,569 A | 4/2000 | Kensey et al. |
| 6,045,570 A | 4/2000 | Epstein et al. |
| 6,048,357 A | 4/2000 | Kontos |
| 6,048,358 A | 4/2000 | Barak |
| 6,054,569 A | 4/2000 | Bennett et al. |
| 6,056,768 A | 5/2000 | Cates et al. |
| 6,056,769 A | 5/2000 | Epstein et al. |
| 6,056,770 A | 5/2000 | Epstein et al. |
| 6,080,183 A | 6/2000 | Tsugita et al. |
| 6,110,184 A | 8/2000 | Weadock |
| 6,120,524 A | 9/2000 | Taheri |
| 6,126,675 A | 10/2000 | Shchervinsky et al. |
| 6,162,240 A | 12/2000 | Cates et al. |
| 6,179,863 B1 | 1/2001 | Kensey et al. |
| 6,183,496 B1 | 2/2001 | Urbanski |
| 6,190,400 B1 | 2/2001 | Van De Moer et al. |
| 6,261,309 B1 | 7/2001 | Urbanski |
| 6,296,632 B1 | 10/2001 | Luscher et al. |
| 6,296,657 B1 | 10/2001 | Brucker |
| 6,296,658 B1 | 10/2001 | Gershony et al. |
| 6,325,789 B1 | 12/2001 | Janzen et al. |
| 6,350,274 B1 | 2/2002 | Li |
| 6,368,300 B1 | 4/2002 | Fallon et al. |
| 6,368,341 B1 | 4/2002 | Abrahamson |
| 6,425,911 B1 | 7/2002 | Akerfeldt et al. |
| 6,461,346 B1 | 10/2002 | Buelna |
| 6,464,712 B1 | 10/2002 | Epstein et al. |
| 6,468,293 B2 | 10/2002 | Bonutti et al. |
| 6,475,177 B1 | 11/2002 | Suzuki |
| 6,475,230 B1 | 11/2002 | Bonutti et al. |
| 6,500,152 B1 | 12/2002 | Illi |
| 6,508,828 B1 | 1/2003 | Akerfeldt et al. |
| 6,524,328 B2 | 2/2003 | Levinson |
| 6,527,734 B2 | 3/2003 | Cragg et al. |
| 6,537,299 B1 | 3/2003 | Hogendijk et al. |
| 6,540,735 B1 | 4/2003 | Ashby et al. |
| 6,569,187 B1 | 5/2003 | Bonutti et al. |
| 6,572,635 B1 | 6/2003 | Bonutti |
| 6,592,608 B2 | 7/2003 | Fisher et al. |
| 6,596,012 B2 | 7/2003 | Akerfeldt et al. |
| 6,596,014 B2 | 7/2003 | Levinson et al. |
| 6,613,070 B2 | 9/2003 | Redmond et al. |
| 6,623,509 B2 | 9/2003 | Ginn |
| 6,632,238 B2 | 10/2003 | Ginn et al. |
| 6,656,207 B2 | 12/2003 | Epstein et al. |
| 6,663,655 B2 | 12/2003 | Ginn et al. |
| 6,682,489 B2 | 1/2004 | Tenerz et al. |
| 6,685,727 B2 | 2/2004 | Fisher et al. |
| 6,699,261 B1 | 3/2004 | Cates et al. |
| 6,712,837 B2 | 3/2004 | Åkerfeldt et al. |
| 6,733,515 B1 | 5/2004 | Edwards et al. |
| 6,743,195 B2 | 6/2004 | Zucker |
| 6,749,621 B2 | 6/2004 | Pantages et al. |
| 6,764,500 B1 | 7/2004 | Muijs Van De Moer et al. |
| 6,780,197 B2 | 8/2004 | Roe et al. |
| 6,790,220 B2 | 9/2004 | Morris et al. |
| 6,818,008 B1 | 11/2004 | Cates et al. |
| 6,860,895 B1 | 3/2005 | Akerfeldt et al. |
| 6,863,680 B2 | 3/2005 | Ashby |
| 6,890,342 B2 | 5/2005 | Zhu et al. |
| 6,890,343 B2 | 5/2005 | Ginn et al. |
| 6,896,692 B2 | 5/2005 | Ginn et al. |
| 6,929,655 B2 | 8/2005 | Egnelov et al. |
| 6,939,363 B2 | 9/2005 | Åkerfeldt |
| 6,942,684 B2 | 9/2005 | Bonutti |
| 6,955,683 B2 | 10/2005 | Bonutti |
| 6,964,658 B2 | 11/2005 | Ashby et al. |
| 6,969,397 B2 | 11/2005 | Ginn |
| 7,001,398 B2 | 2/2006 | Carley et al. |
| 7,008,439 B1 | 3/2006 | Janzen et al. |
| 7,008,440 B2 | 3/2006 | Sing et al. |
| 7,008,441 B2 | 3/2006 | Zucker |
| 7,008,442 B2 | 3/2006 | Brightbill |
| 7,025,776 B1 | 4/2006 | Houser et al. |
| 7,037,323 B2 | 5/2006 | Sing et al. |
| 7,044,916 B2 | 5/2006 | Tenerz et al. |
| 7,083,635 B2 | 8/2006 | Ginn |
| 7,192,436 B2 | 3/2007 | Sing et al. |
| 7,267,679 B2 | 9/2007 | McGuckin, Jr. et al. |
| 7,316,704 B2 | 1/2008 | Bagaoisan et al. |
| 7,322,976 B2 | 1/2008 | Yassinzadeh |
| 7,331,979 B2 | 2/2008 | Khosravi et al. |
| 7,331,981 B2 | 2/2008 | Cates et al. |
| 7,335,220 B2 | 2/2008 | Khosravi et al. |
| 2002/0002889 A1 | 1/2002 | Ashby et al. |
| 2002/0016612 A1 | 2/2002 | Ashby |
| 2002/0198562 A1 | 12/2002 | Akerfeldt et al. |
| 2003/0088271 A1 | 5/2003 | Cragg |
| 2004/0093025 A1 | 5/2004 | Egnelov |
| 2004/0098044 A1 | 5/2004 | Van de Moer et al. |
| 2004/0098046 A1 | 5/2004 | Tenerz et al. |
| 2004/0172059 A1 | 9/2004 | Tenerz et al. |
| 2004/0204741 A1 | 10/2004 | Egnelov et al. |
| 2004/0215232 A1 | 10/2004 | Belhe et al. |
| 2004/0243007 A1 | 12/2004 | Tenerz et al. |
| 2005/0049637 A1 | 3/2005 | Morris et al. |
| 2005/0085852 A1 | 4/2005 | Ditter |
| 2005/0085855 A1 | 4/2005 | Forsberg |
| 2005/0096696 A1 | 5/2005 | Forsberg |
| 2005/0096697 A1 | 5/2005 | Forsberg et al. |
| 2005/0107827 A1 | 5/2005 | Paprocki |
| 2005/0125031 A1 | 6/2005 | Pipenhagen et al. |
| 2005/0137624 A1 | 6/2005 | Fallman |
| 2005/0169974 A1 | 8/2005 | Tenerz et al. |
| 2005/0177189 A1 | 8/2005 | Ginn et al. |
| 2005/0267521 A1 | 12/2005 | Forsberg |
| 2005/0267528 A1 | 12/2005 | Ginn et al. |
| 2006/0004408 A1 | 1/2006 | Morris et al. |
| 2006/0030886 A1 | 2/2006 | Clark |

| | | |
|---|---|---|
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0100664 A1 | 5/2006 | Pai et al. |
| 2006/0142797 A1 | 6/2006 | Egnelov |
| 2006/0173492 A1 | 8/2006 | Akerfeldt et al. |
| 2006/0178682 A1 | 8/2006 | Boehlke |
| 2006/0206146 A1 | 9/2006 | Tenerz |
| 2006/0229672 A1 | 10/2006 | Forsberg |
| 2006/0229673 A1 | 10/2006 | Forsberg |
| 2006/0229674 A1 | 10/2006 | Forsberg |
| 2006/0265006 A1 | 11/2006 | White et al. |
| 2006/0265007 A1 | 11/2006 | White et al. |
| 2006/0265008 A1 | 11/2006 | Maruyama et al. |
| 2007/0032823 A1 | 2/2007 | Tegg |
| 2007/0032824 A1 | 2/2007 | Terwey |
| 2007/0038244 A1 | 2/2007 | Morris et al. |
| 2007/0038245 A1 | 2/2007 | Morris et al. |
| 2007/0073345 A1 | 3/2007 | Pipenhagen et al. |
| 2007/0083231 A1 | 4/2007 | Lee |
| 2007/0083232 A1 | 4/2007 | Lee |
| 2007/0135842 A1 | 6/2007 | Van de Moer et al. |
| 2007/0276433 A1 | 11/2007 | Huss |
| 2008/0065121 A1 | 3/2008 | Kawaura et al. |
| 2008/0071311 A1 | 3/2008 | White et al. |
| 2008/0097521 A1 | 4/2008 | Khosravi et al. |
| 2008/0109030 A1 | 5/2008 | Houser et al. |
| 2008/0114394 A1 | 5/2008 | Houser et al. |
| 2009/0024106 A1 | 1/2009 | Morris |

FOREIGN PATENT DOCUMENTS

| | | |
|---|---|---|
| EP | 1671591 A1 | 6/2006 |
| WO | 8911301 A1 | 11/1989 |
| WO | 2006078578 A2 | 7/2006 |
| WO | 2006124238 A2 | 11/2006 |

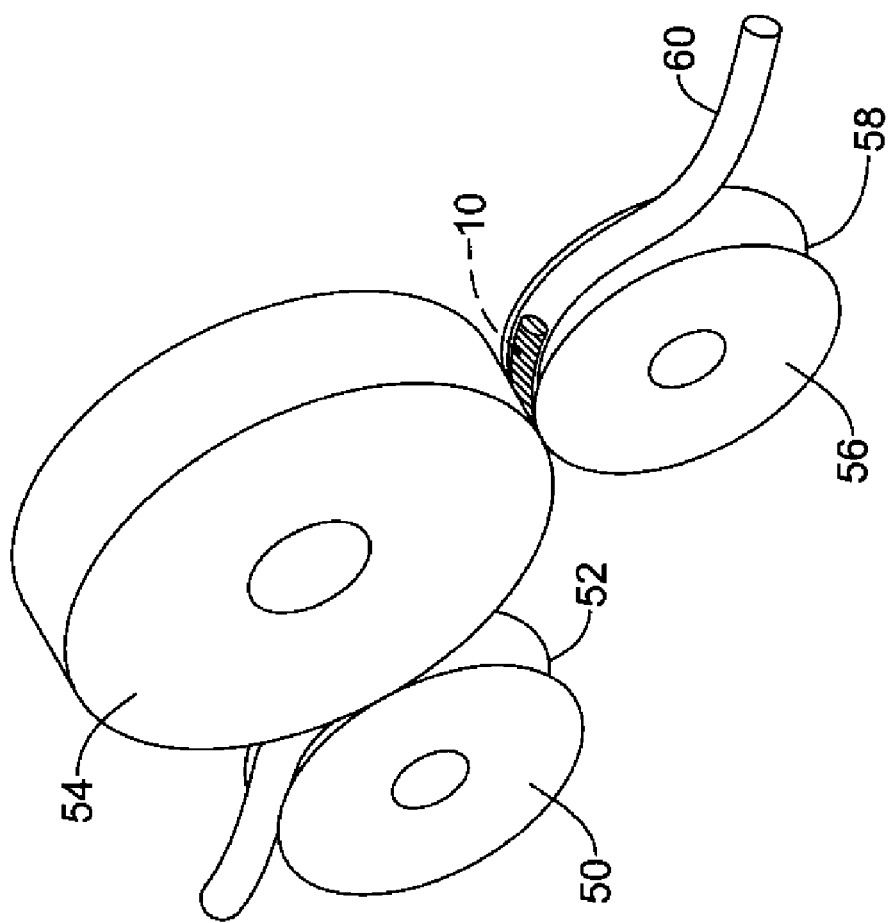

MODIFIED PLUG FOR ARTERIOTOMY CLOSURE

BACKGROUND OF THE INVENTION

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. Further, external pressure to close the vascular puncture site works best when the vessel is close to the skin surface but may be unsuitable for patients with substantial amounts of subcutaneous adipose tissue since the skin surface may be a considerable distance from the vascular puncture site.

There are several approaches to close the vascular puncture site including the use of anchor and plug systems as well as suture systems. Internal suturing of the blood vessel puncture requires a specially designed suturing device. These suturing devices involve a significant number of steps to perform suturing and require substantial expertise. Additionally, when releasing hemostasis material at the puncture site and withdrawing other devices out of the tissue tract, the currently employed approaches to sealing the puncture may only partially occlude the tract thereby allowing blood to seep out of the puncture.

SUMMARY

The disclosure relates to a modified plug for arteriotomy closure comprising an elongated member formed from a bioabsorbable foam having struts defining cells, said elongated member having a length, a distal end, a proximal end, and a longitudinal axis therebetween, wherein the bioabsorbable foam has been modified by radial compression and axial bending sufficient to create at least one axially disposed region in which struts of the foam have been torn or elongated.

In another aspect, the disclosure relates to a method of modifying a plug for arteriotomy closure comprising the steps of providing an elongated member comprising a bioabsorbable foam having struts defining cells, said elongated member having a length, a distal end, a proximal end, a diameter, and a longitudinal axis; compressing at least a portion of the elongated member radially; and bending the elongated member axially until at least some struts of the bioabsorbable foam have been torn or elongated within at least one axially disposed region.

BRIEF DESCRIPTION OF DRAWINGS

FIGS. 4A-B are schematic views of an arteriotomy closure plug during modification.

DETAILED DESCRIPTION

Figure 1:
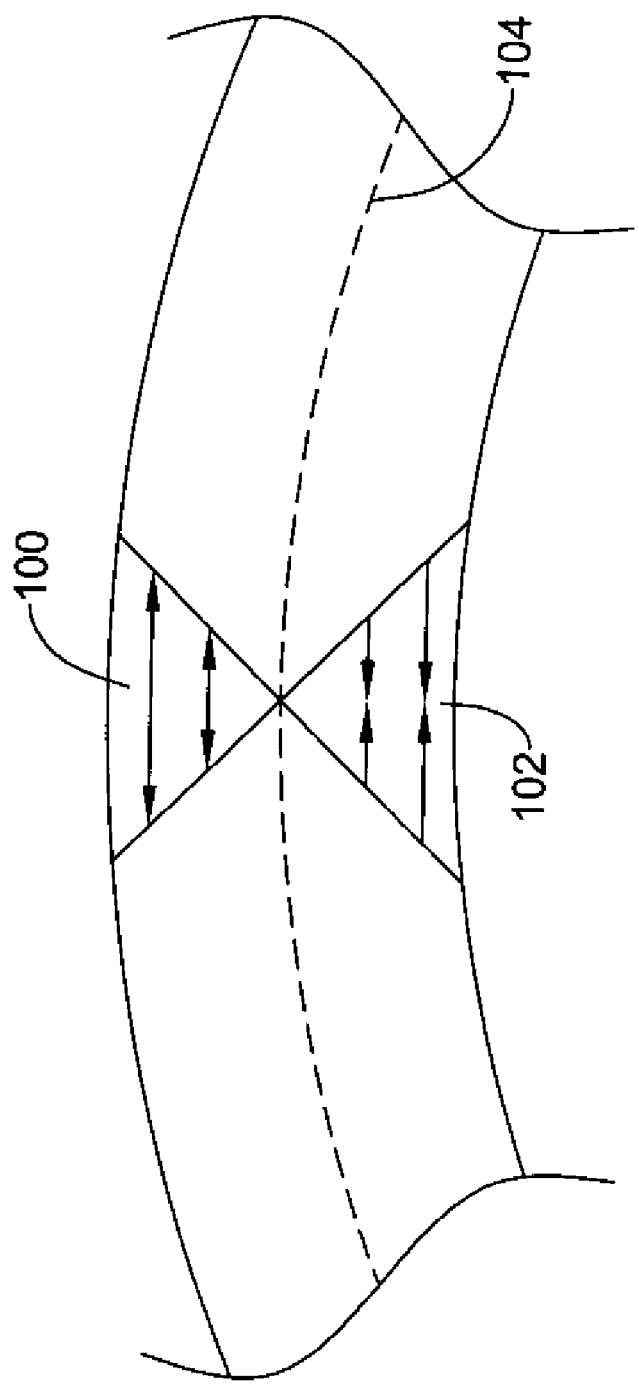
FIG. 1 is schematic view of stresses within a uniform bent rod.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

FIG. 1 schematically illustrates the distribution of tensile and compressive forces which arise during flexure of a uniform rod. The distribution is approximately symmetrical for small deflections with the volume of the compression zone (102) becoming smaller than the volume of the corresponding tension zone (100) at larger deflections. At small deflections, the neutral axis (104) generally corresponds to the center of the rod. Tensile stresses are generally highest in that portion of a curved section having the greatest radius of curvature, sometimes referred to as the outer fiber of the curved rod.

Figure 2:
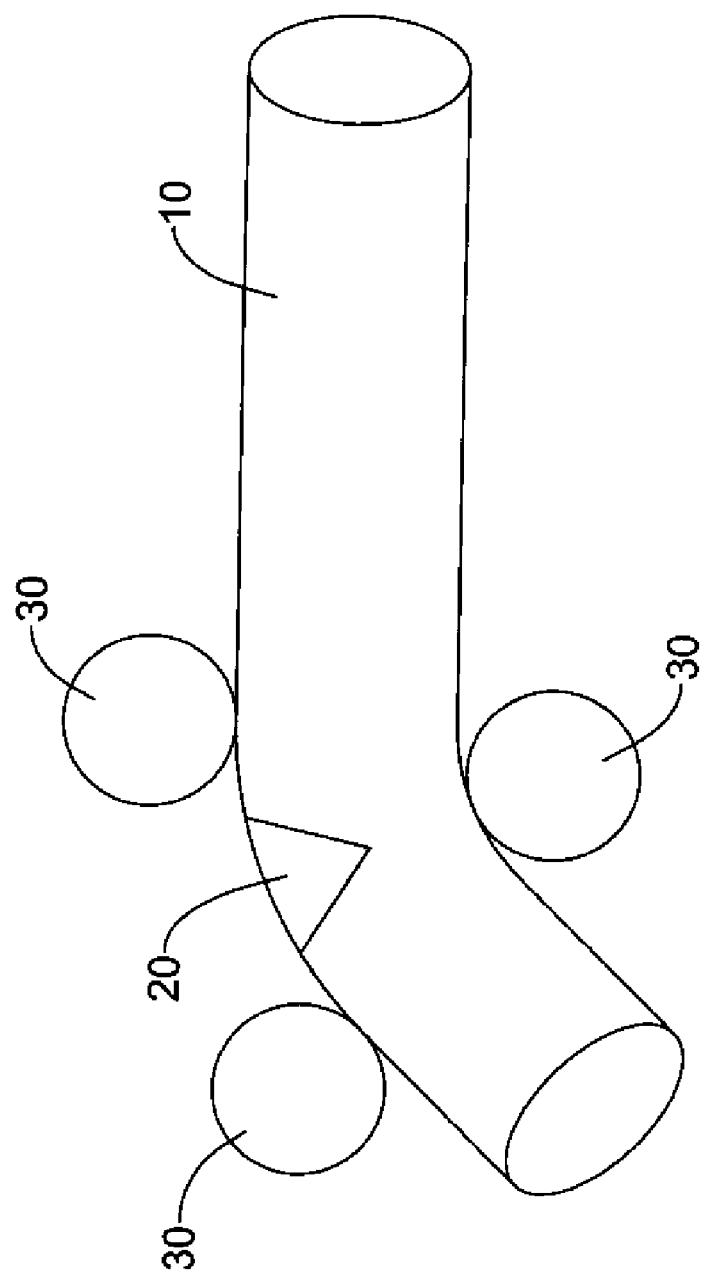
FIG. 2 is a schematic view of an arteriotomy closure plug during modification.
Figure 3:
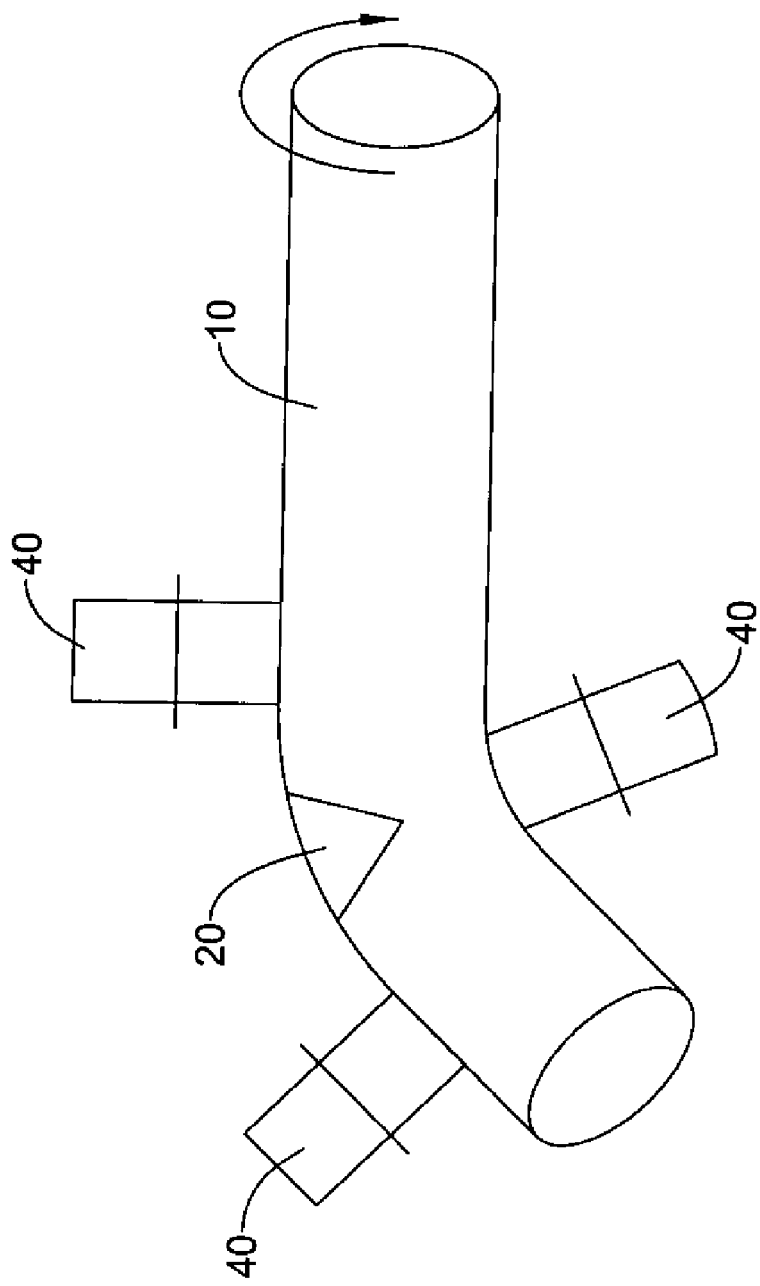
FIG. 3 is a schematic view of an arteriotomy closure plug during modification.

FIGS. 2 and 3 schematically illustrate methods which optionally may be used to elongate an outer fiber of a bioabsorbable foam arteriotomy closure plug (10) in an axial region located along the length of the closure plug. A bioabsorbable foam arteriotomy closure plug which may be modified in this way is disclosed in co-pending application Ser. No. 12/390, 289, filed Feb. 20, 2009 incorporated herein by reference in its entirety. Three-point bending of the arteriotomy closure plug (10) using, for example rods (30) or rollers (40), will create a localized region of tensile stress (20). Appropriate bending methods may also employ deformable tubes partially surrounding the closure plug to facilitate handling of the plug and/or to confine bending forces to a desired region of the plug. Modification of the closure plug material through tearing or elongation of at least some struts within the bioabsorbable foam may occur when the stress applied to individual struts within the bending region becomes greater than the tensile strength of the strut material. Generally strut tearing and/or elongation occurs first and is most prevalent near the outer fiber of the bent plug, where stresses and strains are greatest, and diminishes nearer the center of the plug. Local bending may be accompanied by rotation of the closure plug about the longitudinal axis to create a circumferential band of modified plug material if desired.

Figure 4B:
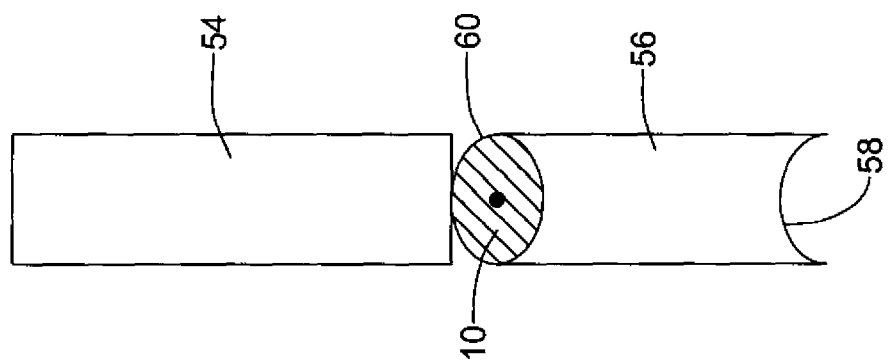

FIGS. 4A-B illustrates an alternate method of generating sufficient tensile stress to tear or elongate at least some struts within a region or regions of a bioabsorbable foam arteriotomy closure plug (10). In this method, a closure plug may be disposed within an optional flexible sheath (60) to facilitate handling of the plug which otherwise may be too short to be manipulated conveniently. The use of a flexible sheath may provide other benefits such as maintaining cleanliness during the manufacturing process or holding the plug in a compressed state prior to insertion into a delivery system. Three generally coplanar rollers (50,54,56) optionally having circumferential grooves (52,58) are arranged such that the perimeter of the central roller (54) extends partially into the gap between the outer rollers (50 and 56) such that the closure plug (10) disposed within the sheath (60) conforms generally to the curvature of the roller (54). The radius of the roller (54) may be selected to be sufficiently small to ensure that at least some of the struts in the outer fiber of the closure plug are sufficiently stressed to cause them to tear or elongate under elongation. The space between the rollers may also be adjusted to provide axial compression of closure plug (10) disposed within the sheath (60) as illustrated in FIG. 4B. During the modification process, one or more of the rollers may be rotated to cause different regions of the closure plug to be exposed to modifying stress levels. In addition to simple translation, the plug may be caused to move back and forth within the nip region between the rollers and/or the plug may be made to rotate about a longitudinal axis. A combination of translation and rotation may be used to provide a helical modified region.

Each of the modification methods described in regard to FIGS. 2-4 is capable of providing at least some radial compression of the closure plug during processing of the plug in addition to the necessary degree of bending. Additional processing elements and/or conventional adjustment of processing conditions may be used to provide additional compression if desired. For example, in the apparatus of FIG. 4B the gap between the central roller (54) and one or both of the outer rollers (50 and 56) may be reduced to provide additional radial compression. In each of the methods described, additional struts may be torn or elongated by repeating the bending operation. One of ordinary skill in the art will appreciate that the details of methods represented in FIGS. 2-4 are illustrative and nonlimiting as other methods of manipulating the closure plug may be used to generate localized bending sufficient to tear or elongate at least some struts within an axial region associated with a closure plug.

It is believed that radial compression of a foam closure plug to a smaller diameter for loading into a delivery sheath, such as that disclosed in co-pending application Ser. No. 12/390,241, filed Feb. 20, 2009 incorporated herein by reference in its entirety, in the absence of at least some strut tearing or elongation, results in an increase in column stiffness which may require more force to axially compress the plug during deployment and may also increase the risk of tearing. To an extent, both the axial compression force required and the risk of tearing may be reduced by introducing modifications which promote buckling of the plug during axial compression. Such modifications are disclosed in co-pending application Ser. No. 12/389,960, filed Feb. 20, 2009 incorporated herein by reference in its entirety. Modification by methods of this disclosure may be used in conjunction with the introduction of buckling promoting features. For example, the disclosed modification may produce a more supple closure plug making it easier to bend at the buckling sites thereby allowing the desired folding to occur with reduced axial force. A combination of the two modification methods may advantageously be applied to locally control column stiffness. In some embodiments, for example, the ends of the closure plug may be left relatively stiff, while localized areas of the plug near the buckling sites may be made more flexible by strut tearing or elongation to further promote folding at those points. Other zoned strut modification patterns are also possible. In yet other embodiments, it may be desirable to subject the entire closure plug to moderate strut modification thereby reducing overall delivery force.

The method of the disclosure is well suited to the modification of foamed arteriotomy closure plugs fabricated, for example, from gelatin or collagen foams. In addition, it may also be useful for modification of various porous closure plugs of the art where breakage of molecular chains may replace tearing or elongating struts within a foam. Although the disclosure generally supposes that the foam being modified is an open-cell foam, it will be apparent to one of ordinary skill in the art that it may also be applied to closed-cell foams and in those applications may result in cell wall rupture at appropriate induced stress levels. In both open-cell foams and closed-cell foams, it is believed that strut modification occurs when an individual strut is elongated beyond its tensile elongation limit. Although strut modification may also be induced by simple axial elongation of the closure plug, such elongation does not generally limit local elongation and may increase the risk of creating a propagating tear leading to failure. The geometry of bending is thought to provide better control of bulk elongation within the region being modified as well as providing a predictable means of locally inducing and limiting strut breakage. For example, strut breakage may be largely confined to the surface of a closure plug thereby preserving core strength and tear resistance surrounding a suture lumen. In some embodiments, strut modification may be induced in a band which is symmetric about the longitudinal axis while in other embodiments strut modification may be confined to a single lateral region resulting in an asymmetric region.

In some embodiments, the local modification of struts by bending may result in the creation of regions having channels which are less resistant to the flow of water or other fluids when compared to adjacent regions in which struts remain modified. In other embodiments, regions including a higher proportion of struts torn or elongated by bending may have a lower resistance to axial bending. In yet other embodiments, both fluid permeability and resistance to bending may be modified in regions containing struts torn or elongated by bending when compared to adjacent regions in which few if any struts have been torn or elongated.

Closure plugs of the disclosure may include other features which modify their performance. In addition to the buckling promoting features mentioned above, the plug may include a suture lumen and a suture which may be used to compress the plug upon deployment and anchor the plug adjacent to the deployment site. The closure plug may include additional components such as a hydrogel, hemostatic material, antimicrobials (antibiotics), growth factors, thrombus enhancing agents, and the like. Such materials may be distributed throughout the plug, may be concentrated in one or more regions of the plug, and/or be applied to the plug as one or more layers. These materials may be used to further modify local stiffness, to limit or promote swelling upon exposure to liquids, and to promote clotting and/or wound healing.

The disclosure also provides a method of modifying a plug for arteriotomy closure. In some embodiments, the method of the disclosure provides radial compression to a region of the closure plug and axial elongation, with attendant strut breakage, of a nearby axially disposed region of the plug. Although not required by all embodiments of the method, the closure plug may be partially or completely enclosed in a tubular member during the bending operation. The tubular member may be either flexible or rigid depending upon the purpose which it serves. Tubular members may be employed to effectively extend the length of the closure plug thereby making it easier to handle and/or transport through a bending apparatus. For example, multiple closure plugs may be sequentially loaded into a flexible closure and advanced to and through an automated bending station such as that illustrated in FIG. 4A. Alternatively, a closure plug may be partially loaded into one or more rigid tubes which tend to limit bending and attendant strut tearing or elongation to a region adjacent to the rigid tube end or to a region between two rigid tubes. The tube ends are not necessarily restricted to being perpendicular to the axis of the tube and may be beveled or curved if desired. Such beveled or curved tube ends may be used to tailor the shape of the modified region by controlling the axial length exposed to local bending induced stresses. In this way, the axial extent of the modified region may be made to vary circumferentially and the resulting asymmetry in permeability may be used to create a plug which tends to bend upon hydration.

In some embodiments, the degree of bulk elongation within the region being bent, and so the approximate degree of strut breakage, may be estimated and controlled by adjusting the mean radius of curvature to which the closure plug is subjected relative to one or both of the diameter of the elongated member and the length of the elongated member. For example, the mean radius of curvature of the bent elongated member within the at least one axial region may be selected to be less than about 2.5 times the diameter of the elongated member or it may be less than about 0.1 times the diameter of the elongated member. Similarly, the mean radius of curvature of the bent elongated member within the at least one axial region may be selected to be less than about 1.0 times the length of the elongated member or it may be less than about 0.1 times the length of the elongated member. These values may need to be adjusted somewhat depending upon the material chosen for the plug and the degree to which the plug has been radially compressed prior to the bending operation. In other embodiments, the geometry of the bend may be selected to provide at least one axial region of elongated member which is elongated by at least about 110% of the yield elongation of the elongated member during the bending step.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A method of modifying a plug for arteriotomy closure comprising the steps of:

providing an elongated member comprising a bioabsorbable foam having struts defining cells, said elongated member having a length, a distal end, a proximal end, a diameter, and a longitudinal axis;

compressing at least a portion of the elongated member radially; and bending the elongated member axially until at least some struts of the bioabsorbable foam have been torn or elongated within at least one axially disposed region.

2. The method of claim 1, wherein the elongated member is contained within a flexible tubular member during the bending step.

3. The method of claim 1, wherein the elongated member is contained within at least one generally rigid tubular member and the bending occurs within a portion of the elongated member which is not contained within the at least one generally rigid tubular member.

4. The method of claim 1, wherein the compressing and bending steps occur simultaneously.

5. The method of claim 1, further comprising rotating the elongated member about the longitudinal axis concurrently with the compressing step.

6. The method of claim 1, further comprising rotating the elongated member about the longitudinal axis concurrently with the bending step.

7. The method of claim 1, wherein the axially disposed region comprises a helix about a portion of the longitudinal axis.

8. The method of claim 1, wherein the compressing and bending steps comprise passing the elongated member between three rollers, wherein a line joining the perimeters of the two outer rollers falls between the perimeter and the axis of the third roller.

9. The method of claim 8, further comprising rotating the elongated member axially as it passes between the three rollers.

10. The method of claim 1, wherein the compressing and bending steps comprise passing the elongated member between three rollers, wherein a line joining the perimeters two outer rollers lies less than a distance equal to the sum of the radius of the third roller and the unmodified diameter of the elongated member from the axis of the third roller.

11. The method of claim 10, further comprising rotating the plug axially as it passes between the three rollers.

* * * * *